United States Patent [19]

Raulerson

[11] Patent Number: 5,045,065
[45] Date of Patent: Sep. 3, 1991

[54] CATHETER INTRODUCTION SYRINGE

[76] Inventor: J. Daniel Raulerson, 1203 Belleville Ave., Brewton, Ala. 36426

[21] Appl. No.: 491,572

[22] Filed: Mar. 15, 1990

Related U.S. Application Data

[63] Continuation-in-part of Ser. No. 326,171, Mar. 20, 1989, abandoned, which is a continuation-in-part of Ser. No. 97,758, Sep. 17, 1987, Pat. No. 4,813,938.

[51] Int. Cl.$^5$ .............................................. A61M 5/00
[52] U.S. Cl. ................................... 604/167; 604/156; 604/169; 604/236
[58] Field of Search ............... 604/167, 169, 156, 124, 604/125, 236, 158, 159, 218

[56] References Cited

U.S. PATENT DOCUMENTS

| | | | |
|---|---|---|---|
| 105,776 | 7/1870 | Cavanaugh . | |
| 1,317,314 | 9/1919 | Powers . | |
| 2,626,604 | 1/1953 | Nadeau | 128/218 |
| 2,711,734 | 6/1955 | Moe | 128/276 |
| 2,936,756 | 5/1960 | Gabriel | 128/218 |
| 3,040,743 | 6/1962 | Naess | 128/216 |
| 3,097,646 | 7/1963 | Scislowicz | 128/214 |
| 3,215,141 | 11/1965 | Podhora | 128/214 |
| 3,308,820 | 3/1967 | Hubbard | 128/216 |
| 3,335,723 | 8/1967 | Waldman | 128/214.4 |
| 3,535,068 | 10/1970 | Larson | 128/218 |
| 3,739,778 | 6/1973 | Monestere | 128/214.4 |
| 3,766,916 | 10/1973 | Moorehead | 128/214.4 |
| 3,851,647 | 12/1974 | Monestere | 128/214.4 |
| 3,853,127 | 12/1974 | Spademan | 128/214.4 |
| 3,859,998 | 1/1975 | Thomas | 128/214.4 |
| 3,920,013 | 11/1975 | Bodzin | 128/214.4 |
| 3,921,729 | 1/1975 | Schmuck | 173/14 |
| 3,978,863 | 9/1976 | Fettel | 128/348 |
| 4,029,104 | 6/1977 | Kerber | 128/348 |
| 4,160,383 | 7/1979 | Rauschenberger | 73/422 R |
| 4,177,814 | 12/1979 | Knepshield | 128/348 |
| 4,200,096 | 4/1980 | Charvin | 128/214.4 |
| 4,233,982 | 11/1980 | Bauer | 128/347 |
| 4,243,034 | 1/1981 | Brandt | 128/214.4 |
| 4,245,635 | 1/1981 | Kontos | 128/214.4 |
| 4,261,357 | 4/1981 | Kontos | 124/214.4 |
| 4,274,408 | 6/1981 | Nimrod | 128/214.4 |
| 4,314,555 | 2/1982 | Sagae | 128/214.4 |
| 4,346,698 | 8/1982 | Hanson | 128/10 |
| 4,356,823 | 11/1982 | Jackson | 128/276 |
| 4,424,833 | 1/1984 | Spector | 137/849 |
| 4,448,195 | 5/1984 | LeVeen | 128/344 |
| 4,464,177 | 8/1984 | McGaughey | 604/168 |
| 4,479,497 | 10/1984 | Fogarty | 128/344 |
| 4,483,340 | 11/1984 | Fogarty | 128/344 |
| 4,517,979 | 5/1985 | Pecenka | 128/325 |
| 4,529,399 | 7/1985 | Groshong | 604/53 |
| 4,601,706 | 7/1986 | Aillon | 604/122 |
| 4,606,347 | 8/1986 | Fogarty | 128/344 |
| 4,610,665 | 9/1986 | Matsumoto | 604/167 |

FOREIGN PATENT DOCUMENTS

| | | |
|---|---|---|
| 2507119 | 9/1976 | Fed. Rep. of Germany . |
| 2415196 | 10/1976 | Fed. Rep. of Germany . |
| 3041229 | 5/1982 | Fed. Rep. of Germany . |
| 2004771 | 11/1969 | France . |
| 507607 | 12/1954 | Italy . |

Primary Examiner—Carl D. Price
Attorney, Agent, or Firm—Arthur W. Fisher, III

[57] ABSTRACT

A catheter introduction syringe for the introduction of a catheter or catheter guide wire into a patient's body, the catheter introduction syringe comprises a hollow syringe barrel including a fluid chamber, a plunger movable between an advanced and retracted position slidably disposed within the fluid chamber, a guide passage formed longitudinally through the hollow syringe barrel and the plunger, the guide passage including an aperture disposed within the fluid chamber and a valve assembly disposed in operative relationship relative to the guide passage to prevent passage of fluid through the guide passage during flushing or aspirating of the catheter introduction syringe or during the introduction or withdrawal of a catheter or catheter guide wire through the guide passage and to permit fluid to flow from the patient's body into the fluid chamber through the aperture the guide passage being configured to maintain the catheter or catheter guide wire in a substantially straight configuration while the catheter or catheter guide wire is disposed within the guide passage.

28 Claims, 9 Drawing Sheets

CATHETER INTRODUCTION SYRINGE

CROSS-REFERENCE

This is a continuation-in-part application of co-pending application Ser. No. 326,171, filed Mar. 20, 1989 now abandoned which is a continuation-in-part application of application Ser. No. 097,171, filed Sep. 17, 1987, now U.S. Pat. No. 4,813,938, issued Mar. 21, 1989.

BACKGROUND OF THE INVENTION

1. Field of the Invention

A catheter introduction syringe comprising a barrel and plunger combination including a guide passage means formed therethrough having a valve assembly disposed therein to prevent the flow of fluid therethrough and permit the introduction of a catheter or catheter guide wire.

2. Description of the Prior Art

The art of introducing a catheter into a patient's body is difficult and often dangerous.

Commonly the central venous catheter placement is performed in the following manner:

(1) The patient is placed in a Trendelenburg position to distend the thoracic veins if the internal jugular or subclavian veins are to be cannulated. The patient is placed in a flat supine position for cannulation of the femoral veins.

(2) Using body landmarks, indentified visually or by palpation, the vein is indentified by aspiration of blood. This is accomplished by gently aspirating a syringe as the needle is advanced. Once blood appears in the syringe presence of the needle within the lumen of the vein is confirmed.

(3) In cannulation, catheter-over-needle catheter is advanced off the needle and down (or up) the vein, or; the syringe is removed from the needle and a catheter is threaded through the needle and into the vein, or; the syringe is removed from the needle and a guidewire is threaded through the needle and into the vein lumen. The needle is then removed leaving the catheter or guidewire in place. If the guidewire is used a catheter is threaded over the guidewire and down the lumen of the vein and the guidewire is removed.

In deep vein cannulation, the deep veins of the chest are exposed to the pressures created by respiration. During the inspiratory phase of respiration negative pressure is transmitted to the veins. In expiration positive pressure is transmitted to the veins. Therefore, if a subclavian or internal jugular vein is exposed to atmospheric pressure blood will pass from the vein during expiration while air will be pulled into the vein during inspiration. It is this latter situation which creates a potentially dangerous condition. If enough air enters the vein and goes to the heart it can result in an air embolus to the brain with the development of a stroke.

Numerous devices have been developed and used for catheter introduction.

For example, U.S. Pat. No. 4,274,408 discloses a syringe-type device for inserting a catheter guide wire into a blood vessel including a syringe in which the plunger has a central passage extending through it. A thin feeder tube including a central passage is slidably disposed in the central passage of the plunger. The plunger passage is normally blocked by a sphere received in a seat provided by a rubber tip on inner edge of the plunger body. The needle is inserted into the blood vessel and the plunger is then partially withdrawn to permit blood to be observed in the body of the syringe for verification of proper needle positioning. The thin feeder tube is then slid through the central passage past the sphere to eject the sphere to open the plunger passage. The thin feeder tube is further advanced to bring the inner end into contact with the end wall of the syringe. In this position, the central passage of the thin feeder tube is aligned and in communication with the needle lumen. A catheter guide wire may then be fed into the blood vessel by sliding it through the central passage of the thin feeder tube and the needle lumen. The device is then removed from the guide wire, and a beveled catheter is inserted over the guide wire in the usual manner.

U.S. Pat. No. 1,317,314 shows a hypodermic syringe including a barrel having an orifice formed therein and a nipple externally threaded and adapted to receive a cap-type needle. A hollow cap is secured to the screw threads to enclose the nipple. In addition, the cap has an end perforation to pass a needle and adapted to hold the mounting collar of the needle against the end of the nipple.

German 24 15 196 discloses a device to ease the intermission of a flexible insert such as a sensor, a catheter or drain tube into a hollow passage such as a vessel or duct in a human or animal body similar to a hypodermic syringe including a piston configured to allow passage of the flexible insert. A viscous medium is contained in the syringe body such that movement of the piston causes explusion of the medium and the insert through a nozzle into the cavity system.

U.S. Pat. No. 4,233,982; U.S. Pat. No. 4,245,635 and U.S. Pat. No. 4,261,357 also show catheter assemblies for intravenous use including a ball or spherical element to selectively operate as a valve sealing means.

U.S. Pat. No. 4,483,340 discloses a dilation catheter including a balloon element configured to be retracted by axial twisting following deflation.

U.S. Pat. No. 4,314,555 shows an intravascular catheter comprising a flexible catheter tube having the proximal end affixed to the distal end of a tubular hub of a catheter. A seal cap is connected to the catheter hub with a flexible tube disposed between the seal cap and catheter hub. The inner wall thereof closely abuts against the outer wall of a cannula which guides the catheter through the blood vessel. A location bar is fixed to a hub of the cannula and protrudes toward the distal end of the catheter. A stopper is mounted on the catheter hub to engage the distal end of the location bar.

U.S. Pat. No. 4,601,706 shows a central venous pressure catheter having a long flexible tube containing at least three channels or lumens. At the tip end of the catheter a balloon surrounds the tube and is inflatable via one of the channels. A distal port and a proximal port in the wall of the tube are located on either side of the balloon, and are connected to the other two channels respectively. The tip end of the catheter may be inserted through a jugular vein into a patient's superior cava vein near the heart. The balloon is inflated to partially obstruct the flow of blood and to increase the blood pressure at a site of surgery at the head or neck of a patient in the upright position to avoid air embolism as well as to prevent bleeding.

U.S. Pat. No. 3,215,141 discloses an apparatus for use in intravenous introduction of a fluid comprising an elongate hollow needle of uniform inner and outer diameter. One end of the needle is formed to provide a sharpened edge for making a vein puncture. A tubular needle holder is removably mounted upon the opposite end of the needle. A sleeve is fitted over the needle holder. A pliable sac is secured at one end to the outer surface of the sleeve and extends rearwardly therefrom. The opposite end of the sac is sealed. A flexible catheter is positioned within the sac with one end in the needle and extendable outwardly of thereof by manipulation through the sac. The uniform outer diameter of the needle permits positioning flatly against a patient's body after withdrawal of the needle from the vein puncture and removal of the needle holder from the needle.

U.S. Pat. No. 4,517,979 shows a detachable balloon catheter comprising a sealing valve assembly having an elongated passageway extending therethrough. An inflatable balloon having a mouth portion is bonded to the periphery of the sealing valve assembly. A small diameter cannula having a distal end which extends through the passageway in the sealing valve assembly. The small diameter cannula includes a connector terminal on the proximal end which is adapted to be coupled to a source of fluid pressure. The sealing valve assembly includes a valve mechanism which permits the passage of the cannula through the passageway but prevents the flow of fluid through the passageway when the cannula is removed.

German 3,042,229 teaches forming a catheter guide element into two portions having two flow passages at either end of a valve cavity including two valve seats and two slotted valve elements together with the use of conical portions on the various elements to assist in guiding the catheter element.

U.S. Pat. No. 4,160,383 shows a unitary vent-valve assembly, useful in urological applications.

U.S. Pat. No. 2,936,756; U.S. Pat. No. 3,097,646; U.S. Pat. No. 3,308,820; U.S. Pat. No. 3,766,916; U.S. Pat. No. 3,853,127; U.S. Pat. No. 3,859,998; U.S. Pat. No. 4,029,104; U.S. Pat. No. 4,177,814; U.S. Pat. No. 4,200,096; U.S. Pat. No. 4,346,698; U.S. Pat. No. 4,424,833; U.S. Pat. No. 4,529,399; U.S. Pat. No. 4,606,347; U.S. Pat. No. 4,610,665 and France 2,004,771 show various syringes or medical instruments employing elastomeric plugs or membranes as seals or valves in combination with syringes.

U.S. Pat. No. 3,739,778 and U.S. Pat. No. 3,851,647 disclose catheter introduction systems using removable plugs to selectively seal fluid or catheter channels.

U.S. Pat. No. 105,776; U.S. Pat. No. 2,711,734 and U.S. Pat. No. 4,356,823 disclose suction control in valve elements movable to selectively control the flow of fluid through a valve body.

U.S. Pat. No. 4,243,034 and U.S. Pat. No. 4,464,177 show clamping structures to seal or control the flow of fluid.

Additional examples of the prior art are shown in U.S. Pat. No. 2,626,604; U.S. Pat. No. 3,040,743; U.S. Pat. No. 3,335,723; U.S. Pat. No. 3,535,068; U.S. Pat. No. 3,920,013; U.S. Pat. No. 3,978,863; U.S. Pat. No. 4,448,195; U.S. Pat. No. 4,479,497; German 2,415,196; German 2,507,119 and Italy 507,607.

SUMMARY OF THE INVENTION

The present invention relates a catheter introduction syringe and method for the introduction of a catheter or catheter wire into a patient's body comprising a hollow syringe barrel having a plunger slidably disposed therein. The catheter introduction syringe is capable of functioning as a standard air tight syringe as well as a device to introduce a catheter with the minimum resistance to the guide wire or catheter permitting tactile feel during introduction of the guide wire or catheter into the patient's body.

The plunger comprises first and second plunger element and a valve recess cooperatively formed therebetween to operatively house a valve assembly.

The first plunger element includes a first centrally disposed channel formed therethrough and a first valve seat formed therethrough. The second plunger element includes a second centrally disposed channel formed therethrough and a second valve seat formed therein.

The first and second valve seats cooperatively form the valve recess to receive the valve assembly therein. The valve assembly comprises a first and second valve element cooperatively forming a valve chamber therebetween. A normally closed centrally disposed slit or aperture is formed in the center of each valve element.

The hollow syringe barrel supports a needle affixed to the tip thereof. The needle includes an exterior portion extending outwardly from the tip of the hollow syringe barrel and an interior portion having an aperture formed therethrough adjacent the tip of the hollow syringe barrel and extending into the interior of the hollow syringe barrel such that at least a portion of the interior portion is at least partially disposed within the first centrally disposed channel at all times during use.

In use the catheter introduction syringe is aspirated by the retraction of the plunger permitting fluid to pass into the interior of the syringe barrel through the aperture formed on the interior needle portion. During this aspiration, air is prevented from entering the valve chamber by the second valve element. Once aspirated, the catheter introduction syringe may then be flushed. While flushing, the first valve element prevents liquid from passing through the first centrally disposed channel into the valve chamber. Thus the catheter introduction syringe functions as an ordinary syringe.

Then a catheter or catheter guide wire may be passed through the catheter introduction syringe and into the blood vessel or body. The catheter or catheter guide wire passes through the centrally disposed slits or apertures formed within the valve elements which form a seal therewith to prevent either liquid or air from passing through the valve chamber during the introduction of the catheter or catheter guide wire.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
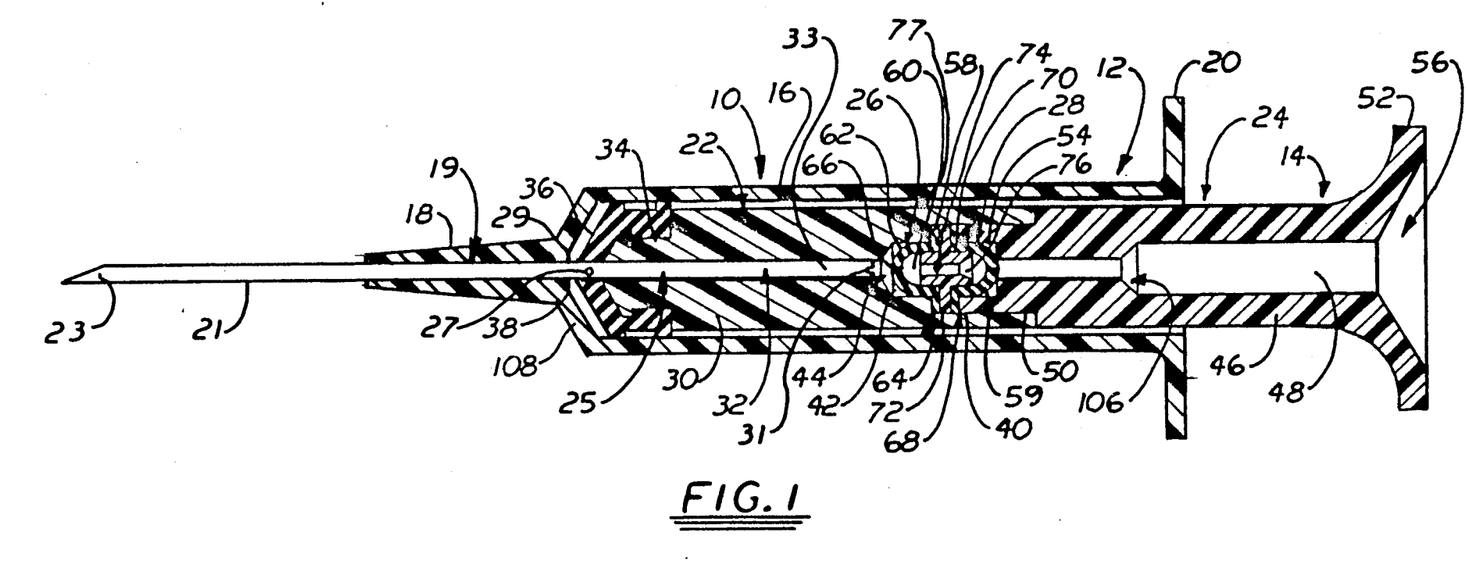
FIG. 1 is a cross-section side view of the catheter introduction syringe with the plunger advanced.
Figure 2:
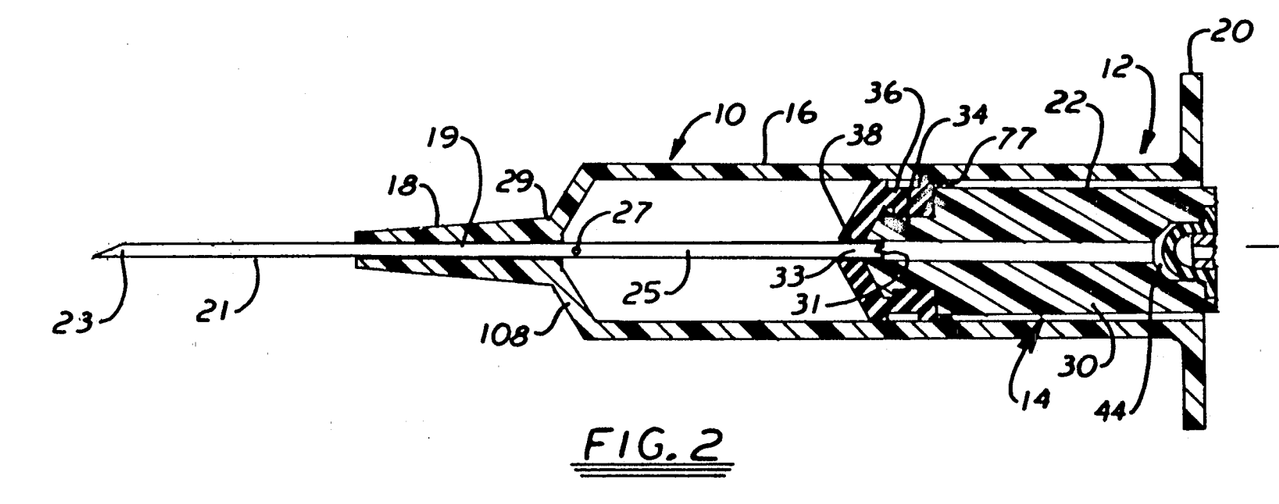
FIG. 2 is a partial cross-sectional side view of the catheter introduction syringe with the plunger retracted.

As shown in FIGS. 1 and 2, the present invention relates a catheter introduction syringe generally indicated as 10 for the introduction of a catheter or catheter wire into a patient's body comprising a hollow substantially cylindrical syringe barrel generally indicated as 12 having a substantially cylindrical plunger generally indicated as 14 slidably disposed therein. As described more fully hereinafter, the catheter introduction syringe 10 is capable of functioning as a standard air tight syringe as well as a device to introduce a catheter or catheter guide wire with minimum resistance to the catheter guide wire or catheter permitting tactile feel during introduction of the guide wire or catheter into the patient's body. In particular, the catheter introduction syringe comprises a hollow syringe barrel including a fluid chamber and a plunger movable between an advanced and retracted position slidably disposed within the fluid chamber. A guide passage means including an aperture disposed the fluid chamber is formed longitudinally through the hollow syringe barrel and plunger. A valve assembly is disposed in operative relationship relative to the guide passage means to prevent passage of fluid through the guide passage means during flushing or aspirating of the catheter introduction syringe or during the introduction or withdrawal of a catheter or catheter guide wire through the guide passage means and to permit fluid to flow from the patient's body into the fluid chamber through the aperture. The guide passage means is configured to maintain the catheter or catheter guide wire in a substantially straight configuration while the catheter or catheter guide wire is disposed within the guide passage means.

The hollow substantially cylindrical syringe barrel 12 comprises a hollow substantially cylindrical body 16 having a hollow barrel tip 18 to support a needle generally indicated as 19 and a finger grasping element 20 formed on opposite ends thereof. The needle 19 comprises a first or exterior portion 21 including a piercing point 23 extending outwardly from the hollow barrel tip 18 and and a second or interior portion 25 extending inwardly from the inner end of the first portion 21 into the interior of the hollow substantially cylindrical syringe barrel 12. An aperture 27 is formed through the second portion 25 adjacent the inner end 29 of the hollow barrel tip 18; while, a conical alignment recess 31 is formed on the inner end 33 of the second interior portion 25.

The substantially cylindrical plunger 14 comprises first and second plunger elements generally indicated as 22 and 24 respectively and a valve recess generally indicated as 26 cooperatively formed therebetween to operatively house a valve assembly generally indicated as 28 therein.

The first plunger element 22 comprises a first substantially cylindrical body 30 having a first centrally disposed channel 32 formed therethrough. One end of the first substantially cylindrical body 30 includes a reduced portion 34 to receive a plunger seal 36 having a centrally disposed seal aperture 38 formed therein, while the opposite end thereof includes a countersunk recess 40 to receive a portion of the second plunger element 24. A first valve seat 42 having a conical alignment recess 44 is formed between the countersunk recess 40 and the first centrally disposed channel 32.

The second plunger element 24 comprises a second substantially cylindrical body 46 having a second centrally disposed channel 48 formed therethrough. The inner end of the second substantially cylindrical body 46 includes a reduced portion 50 to be received within the countersunk recess 40 of the first substantially cylindrical body 30, while the opposite end includes a thumb element or rest 52 having a conical alignment guide recess 56 formed therein. A second valve seat 54 is formed on the inner end of the reduced portion 50 of the second substantially cylindrical body 46.

The first and second valve seats 42 and 54 cooperatively form the valve recess 26 to receive the valve assembly 28 therein. The valve assembly 28 comprises first and second one-way valve elements generally indicated as 58 and 59 respectively to cooperatively form a valve chamber 60 therebetween. Valve elements 58 and 59 comprise a flexible resilient hollow substantially hemispheric member 62 having an annular flange 64 formed about the periphery thereof. A normally closed centrally disposed slit or aperture 66 is formed in the center of each flexible resilient hollow substantially hemispheric member 62. To limit movement or deflection of the first and second valve elements 58 and 59 and maintain the sealing integrity thereof, a rigid valve support element generally indicated as 68 is disposed within the valve chamber 60. The rigid valve support element 68 comprises a substantially cylindrical body 70 having an annular flange 72 formed about the mid-portion thereof. The annular flange 72 is disposed between the annular flanges 64. A centrally disposed channel 74 including a conical alignment recess 76 is formed through the substantially cylindrical body 70. The conical alignment guide recess 56, tapered alignment guide 106, conical alignment recess 76, conical alignment recess 44 and conical alignment recess 31 cooperatively form a catheter alignment means.

As shown in FIG. 1 when the substantially cylindrical plunger 14 is fully advanced within the hollow substantially cylindrical syringe barrel 12, the major portion of the second or interior portion 25 of the needle 19 is disposed within the first centrally disposed channel 32 with the inner end 33 disposed adjacent the valve assembly 28.

In use the catheter introduction syringe 10 is aspirated by the retraction of the substantially cylindrical plunger 14 as shown in FIG. 2 permitting fluid to pass into the interior of the substantially cylindrical syringe barrel 12 through the aperture 27. During aspiration air is prevented from entering the valve chamber 60 by the second valve element 59. Once aspirated, the catheter introduction syringe 10 may then be flushed. While flushing, the first valve element 58 prevents liquid from passing through the first centrally disposed channel 32 into the valve chamber 60. Thus the catheter introduction syringe 10 functions as an ordinary syringe.

As shown in FIG. 2 when the substantially cylindrical plunger 14 is retracted, the inner end of the needle 19 remains disposed within the first centrally disposed channel 32. A plunger stop 77 is formed on the interior of the substantially cylindrical body 16 to engage the plunger seal 36 to limit retraction of the substantially cylindrical plunger 14 when the substantially cylindrical plunger 14 is retracted. In this configuration a catheter or catheter guide wire may be passed through the catheter introduction syringe 10 and into the blood vessel or body cavity using the catheter aligned means. The catheter or guide wire passes through the centrally disposed slots or apertures 66 formed in the first and second valve elements 58 and 59 which form a seal therewith to prevent either liquid or air from passing through the valve chamber 60 during the introduction of the catheter of guide wire.

Figure 11:
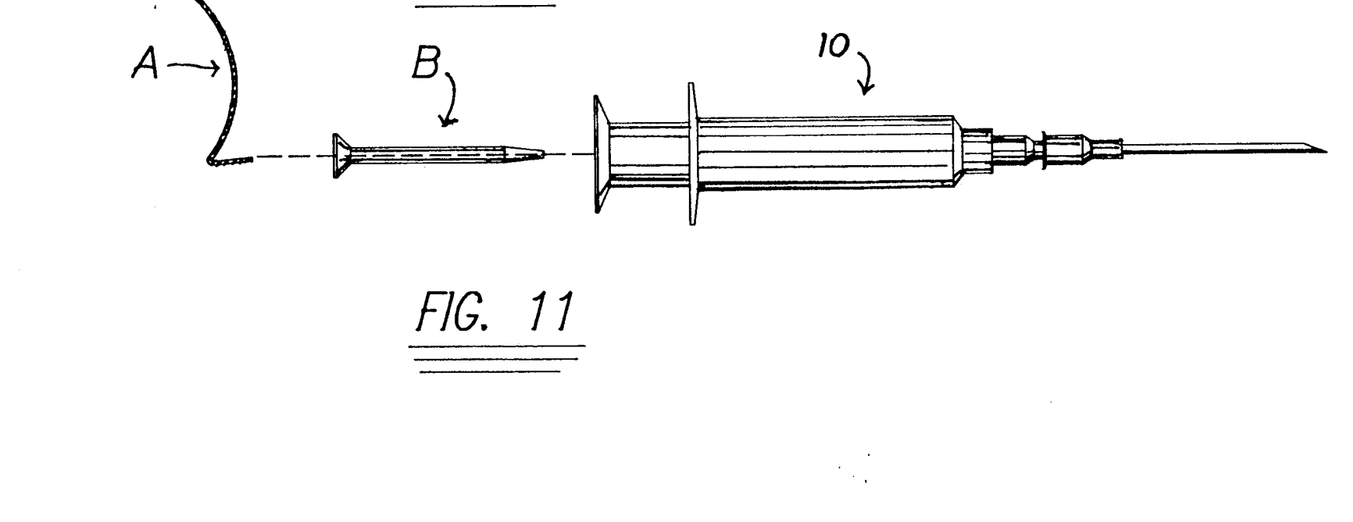
FIG. 11 is a schematic view of a J-tipped catheter guide wire, wire introducer and catheter introduction syringe.

As schematically shown in FIG. 11, this structure is particularly suitable for use with a J-tipped catheter guide wire A. Specifically a straightened J-tipped catheter guide wire A may be inserted into the catheter introduction syringe 10 through a wire introducer B and held in the straightened position while passing therethrough. Without the guide passage means, the J-tipped catheter guide wire A would return to the original J-shape within the catheter introduction syringe 10. This would prevent the J-tipped catheter guide wire A from exiting the catheter introduction syringe 10 precluding insertion into the patient.

Figure 3:
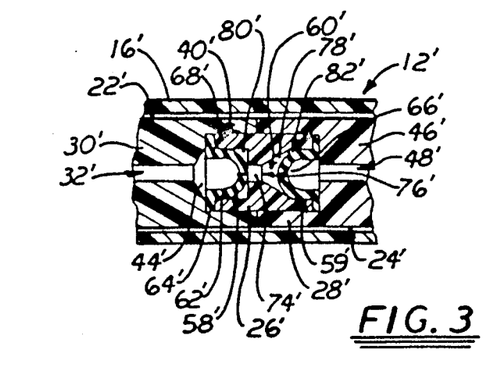
FIG. 3 is a cross-sectional side view of an alternate embodiment of the valve assembly.

An alternate embodiment of the valve assembly 28' is shown in FIG. 3. The first plunger element 22' comprises a first substantially cylindrical body 30' having a first centrally disposed channel 32' formed therethrough. One end thereof includes a countersunk recess 40' having a conical alignment recess 44' formed between the countersunk recess 40' and the first centrally disposed channel 32'. The second plunger element 24' comprises a second substantially cylindrical body 46' having a second centrally disposed channel 48' formed therethrough. The inner end of the second substantially cylindrical body 46' includes a countersunk recess 78'.

The countersunk recesses 40' and 78' cooperatively form the valve recess 26' to receive the valve assembly 28' therein. The valve assembly 28' comprises first and second one-way valve elements generally indicated as 58' and 59' respectively disposed within a first and second valve seat generally indicated as 80' and 82' respectively cooperating forming a valve chamber 60' therebetween.

First and second valve elements 58' and 59' comprise a flexible resilient hollow substantially hemispheric member 62' having an annular flange 64' formed about the periphery thereof. A normally closed centrally disposed slit or aperture 66' is formed in the center of each flexible resilient hollow substantially hemispheric member 62'. To limit movement or deflection of the first and second valve elements 58' and 59' and maintain the sealing integrity thereof, the first and second valve seats 80' and 82' are formed within a rigid valve support element generally indicated as 68' disposed within the valve recess 26'. The rigid valve support element 68' includes a centrally disposed channel 74' extending between the first and second valve seat 80' and 82'. A conical alignment recess 76' is formed within the rigid valve support element 68'. A conical alignment guide recess shown as 56 in FIG. 1, a conical alignment recess 76' and conical alignment recess 44' cooperatively form a catheter alignment means.

The alternate embodiment of the valve assembly 28' shown in FIG. 3 functions similarly to that shown in FIGS. 1 and 2 as described above.

Figure 4:
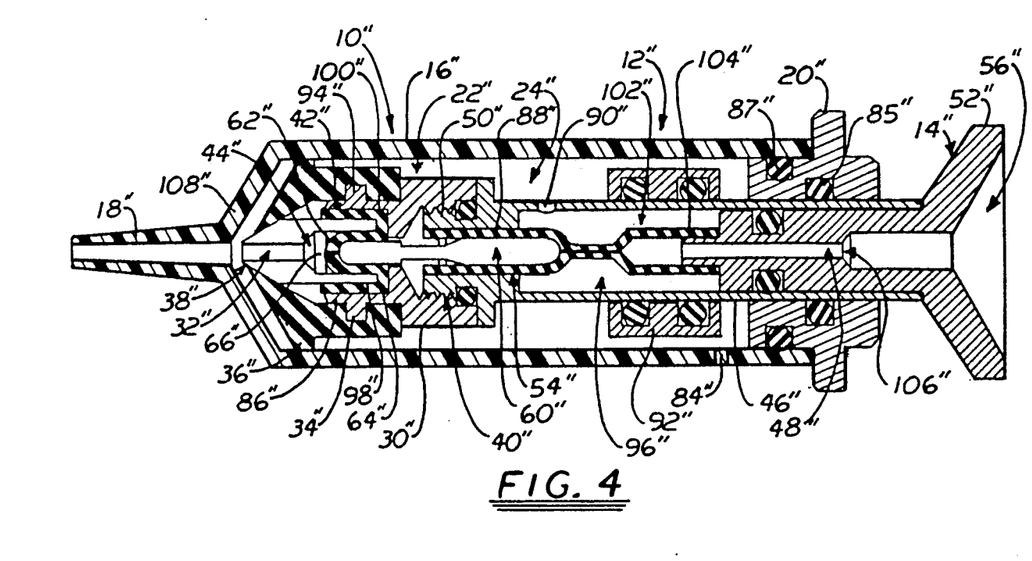
FIG. 4 is a cross-sectional side view of an alternate embodiment of the catheter introduction syringe.

FIG. 4 shows another alternate embodiment of FIGS. 1 and 2 of the catheter introduction syringe 10". The hollow substantially cylindrical syringe barrel 12" comprises a hollow substantially cylindrical body 16" having a hollow barrel tip 18" to receive the needle 19 as described with reference to FIGS. 1 and 2 and a finger grasping element 20" formed on opposite ends thereof. A barrel vent 84" is formed through the sidewall of the hollow substantially cylindrical body 16 preferably near the finger grasping element 20". The finger grasping element 20" further includes a syringe barrel sealing means comprising inner and outer sealing elements indicated as 85" and 87" respectively to form air tight seals between the substantially cylindrical plunger 14" and finger grasping element 20" and between the finger grasping element 20" and the hollow substantially cylindrical syringe barrel 12" respectively.

The substantially cylindrical plunger 14" comprises first and second plunger elements generally indicated as 22" and 24" respectively and a valve recess means to operatively house a valve assembly means.

The first plunger element 22" comprises a first substantially cylindrical body 30" having a first centrally disposed channel 32" formed therethrough. One end of the first substantially cylindrical body 30" includes a reduced portion 34" to receive a plunger seal 36" having a centrally disposed seal aperture 38" formed therein, while the opposite end thereof includes a countersunk recess 40" to receive a portion of the second plunger element 24". A first valve seat 86 including a conical alignment recess 44" is formed in the first plunger element 22".

The second plunger element 24" comprises a second substantially cylindrical body 46" having a second centrally disposed channel 48" formed therethrough. The inner end of the second substantially cylindrical body 46" includes a reduced portion 50" to be received within the countersunk recess portion 40" of the first substantially cylindrical body 30", while the opposite end includes a thumb element or rest 52" having a conical alignment guide recess 56" formed therein. A second valve seat 88" is formed on the inner end of the reduced portion 50" of the second substantially cylindrical body 46". A plunger vent 90" is formed through the side wall of the second plunger element 24". A plunger vent seal 92" is slidably mounted on the second substantially cylindrical body 46" to selectively seal the plunger vent 90" as described more fully hereafter.

The first and second valve seats 86" and 88" cooperatively form the valve recess means to receive a portion of the valve assembly means therein. The valve assembly means comprises a first and second valve element generally indicated as 94" and 96" respectively to cooperatively form a valve chamber 60" therebetween. The first valve element 94" comprises a flexible resilient hollow substantially hemispheric member 62" having an annular flange 64" formed about the periphery thereof. A normally closed centrally disposed slit or aperture 66" is formed in the center of the flexible resilient hollow substantially hemispheric member 62". A substantially cylindrical skirt 98" is formed on the annular flange 64" to limit movement or deflection of the first valve element 94" and maintain the sealing integrity thereof by engaging the sidewall 100" of the first valve seat 86". The second valve element 96" comprises a flexible resilient hollow tube generally indicated as 102" extending between the second valve seat 88" and a coupling element 104" extending from the inner end of the thumb element or rest 52". The cross-sectional diameter of the mid-portion of the flexible resilient hollow tube 102" is reduced to form the normally closed centrally disposed slit or aperture 96". The conical alignment recess 56", tapered alignment guide 106" and conical alignment recess 44" cooperatively form a catheter alignment means.

In use, the substantially cylindrical plunger 14" is inserted into the substantially cylindrical syringe barrel 12" with the plunger vent seal 92" preferably against the finger grasping element 20" with the plunger vent 90" open. The substantially cylindrical plunger 14" is then fully retracted as barrel vent 84" is occluded. The positive pressure created inside the hollow substantially cylindrical syringe barrel 12" is transmitted into the interior of the second plunger element 24" through the plunger vent 90". The plunger vent 90" is then sealed by the plunger vent seal 92" and the positive pressure within the interior of the second plunger element 24" maintained when the second plunger element 24" is fully retracted. When the barrel vent 84" is opened to atmospheric pressure, the plunger vent seal 92" remains over the plunger vent 90" as the catheter introduction syringe 10" is aspirated or flushed. The positive pressure within the second plunger element 24" maintains the sealing integrity of the second valve element 96".

When the catheter introduction syringe 10" is aspirated fluid passes into the hollow substantially cylindrical barrel 12" through the hollow barrel tip 18". During this aspiration air is prevented from entering the valve chamber 60" by the second valve element 96". Once aspirated, the catheter introduction syringe 10" may then be flushed. While flushing, the first valve element 94" prevents liquid from passing through the first centrally disposed channel 32" into the valve chamber 60". Thus the catheter introduction syringe 10" functions as an ordinary syringe.

Then a catheter guide wire or catheter can be passed through the catheter introduction syringe 10" and into a blood vessel or body cavity as previously described.

The catheter alignment means may further include a conical alignment recess 106" formed in the second centrally disposed channel 48" and a conically shaped inner end 108" of the hollow substantially cylindrical syringe barrel tip 18".

Figure 5:
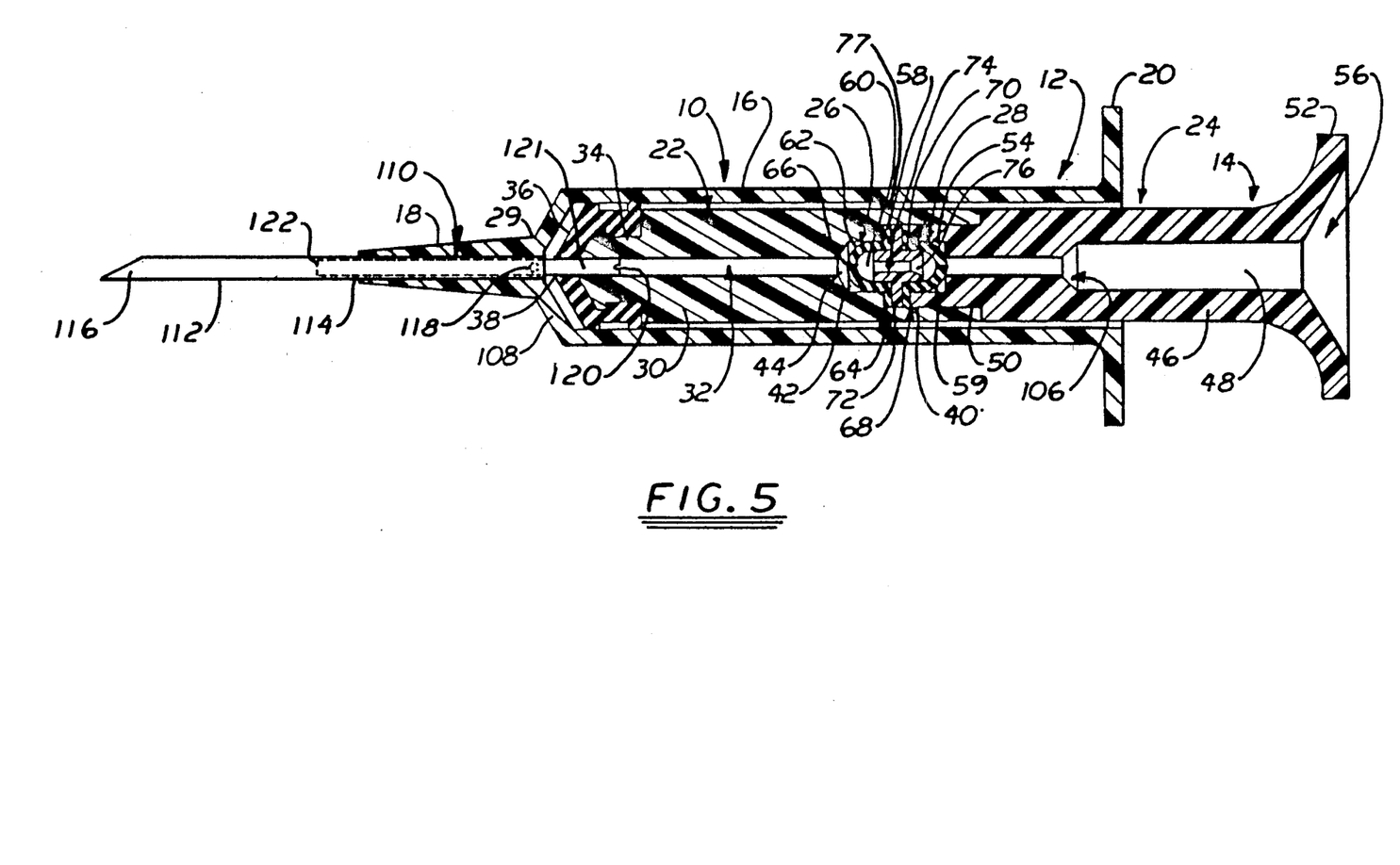
FIG. 5 is a partial cross-sectional side view of an alternate embodiment of the needle with the plunger advanced.
Figure 6:
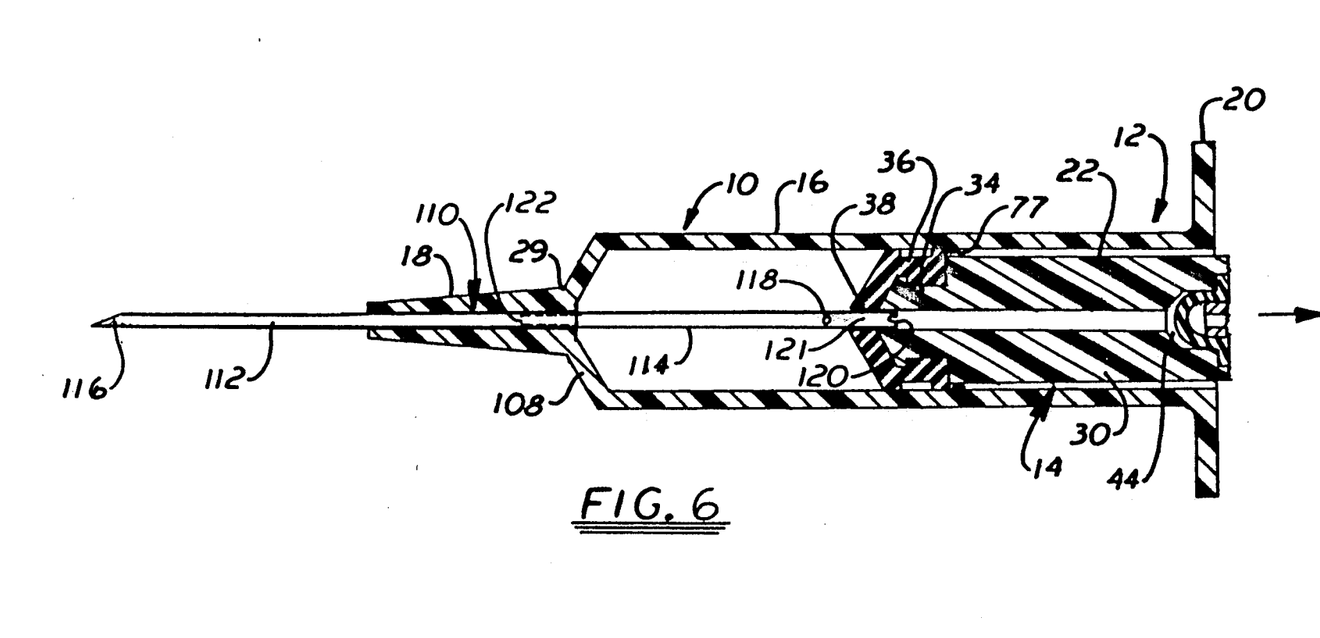
FIG. 6 is a partial cross-sectional side view of the alternate embodiment of the needle of FIG. 5 with the plunger retracted.

FIGS. 5 and 6 show an alternate embodiment of a two piece needle generally indicated as 110 including a first or exterior and second or interior portion or section indicated as 112 and 114 respectively. The first portion 112 including a piercing point 116 is affixed to the hollow barrel tip 18. The first portion 112 extends outwardly from the hollow barrel tip 18. The second portion 114 is affixed to the substantially cylindrical plunger 14 and slidably disposed within the first portion 112. An aperture 118 is formed through the second portion or section 114 immediately adjacent the inner end of the plunger seal 36; while, a conical alignment recess 120 is formed on the inner end 121 of the second portion 114.

As shown in FIG. 5 when the substantially cylindrical plunger 14 is fully advanced within the hollow substantially cylindrical syringe barrel 12, the major portion of the second or interior portion 114 is disposed within the first or exterior portion 112 with the outer end 122 of the second or interior portion 114 disposed within the first or exterior portion 112.

As shown in FIG. 6 when the substantially cylindrical plunger 14 is retracted, the outer end 122 of the second or interior portion 114 remains disposed within the first or exterior portion 112. A plunger stop 77 is formed on the interior of the hollow substantially cylindrical body 16 to engage the plunger seal 36 to limit retraction of the substantially cylindrical plunger 14 when the substantially cylindrical plunger 14 is retracted.

Thus as shown in FIGS. 5 and 6, the outer end 122 of the second portion 114 is disposed within the first portion 112 in either the advanced or retracted position of the hollow substantially cylindrical syringe barrel 12 relative to the substantially cylindrical plunger 14.

Otherwise the operation of the embodiment shown in FIGS. 5 and 6 is similar to the embodiment shown in FIGS. 1 and 2. These two embodiments are particularly suited for subclavian or internal jugular vein use.

Figure 7:
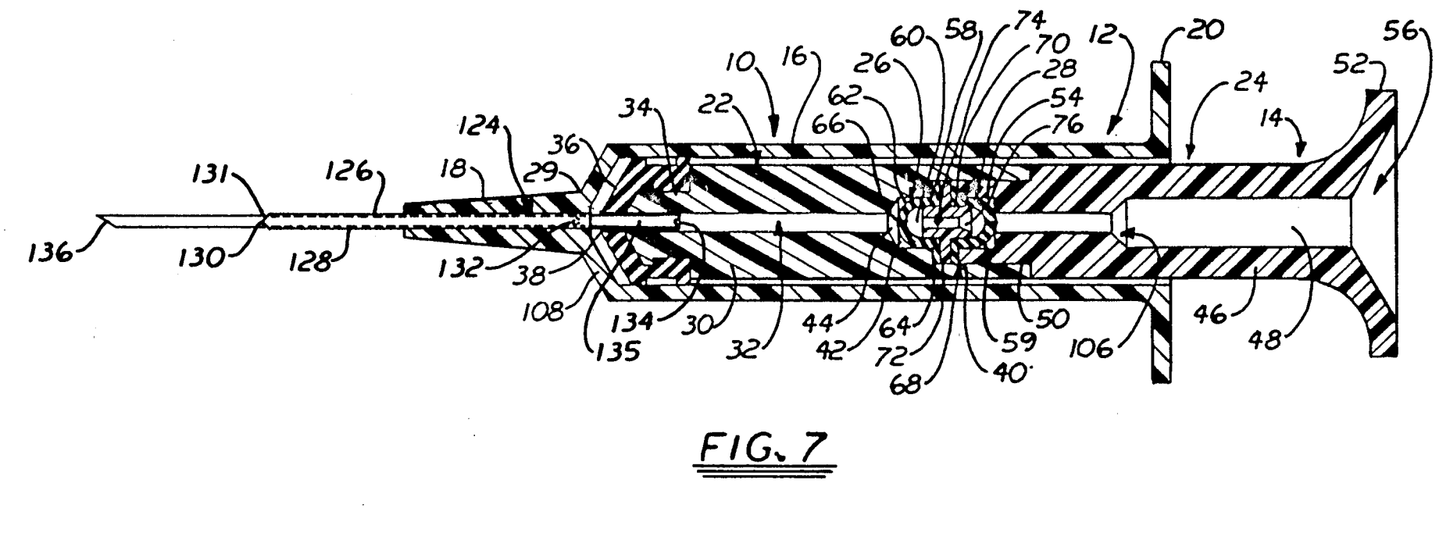
FIG. 7 is a partial cross-sectional side view of another alternate embodiment of the needle with the plunger advanced.
Figure 8:
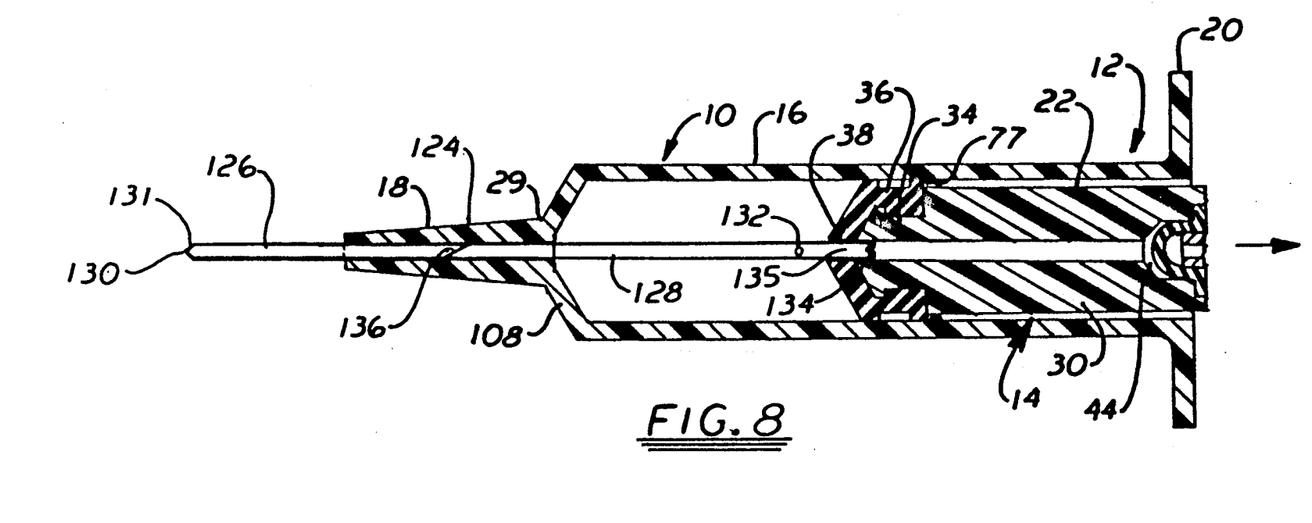
FIG. 8 is a partial cross-sectional side view of the alternate embodiment of the needle of FIG. 7 with the plunger retracted.

FIGS. 7 and 8 show another alternate embodiment of a two piece needle generally indicated as 124 including a first or exterior and second or interior portion indicated as 126 and 128 respectively. The first portion 126 including a blunt point 130 is affixed to the hollow barrel tip 18 The blunt point 130 may include a conically tapered end 131. The first portion 126 extends outwardly from the hollow barrel tip 18. The second portion 128 is affixed to the substantially cylindrical plunger 14 and slidably disposed within the first portion 126. An aperture 132 is formed through the second portion 128 immediately adjacent the inner end of the plunger seal 36; while, a conical alignment recess 134 is formed on the inner end 135 of the second portion 128. A piercing point 136 is formed on the outer end of the second portion 128.

As shown in FIG. 7 when the substantially cylindrical plunger 14 is fully advanced within the hollow substantially cylindrical syringe barrel 12, the major portion of the second or interior portion 128 is disposed within the first or exterior portion 126 with the piercing point 136 extending outwardly from the blunt point 130.

As shown in FIG. 8 when the substantially cylindrical plunger 14 is retracted, the piercing point 136 is disposed within the first or exterior portion 126. A plunger stop 77 is formed on the interior of the substantially cylindrical body 16 to engage the plunger seal 36 to limit retraction of the substantially cylindrical plunger 14.

Since the piercing point 136 extends outwardly of the blunt point 130 when in the advanced position, the piercing 28 point 136 introduces the needle 124 into the patient's body.

The piercing point 136 is then retracted into the first portion 126 to permit rotation of the catheter introduction syringe 10 to prevent laceration of the patient's blood vessel as the two piece needle 124 is axially aligned with the blood vessel to facilitate introduction of the catheter or catheter guide wire into the blood vessel. The catheter or catheter guide wire may then be introduced as previously described.

Thus this embodiment is particularly suited for femoral use.

Figure 9:
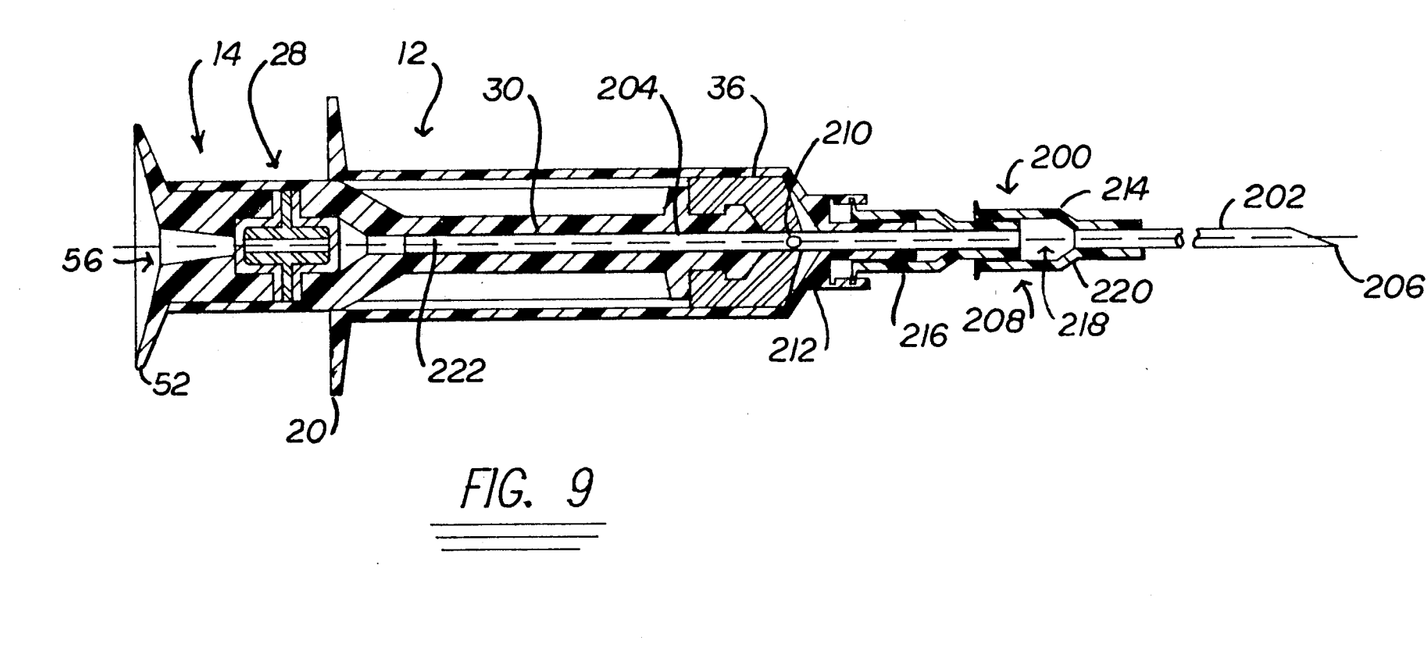
FIG. 9 is a cross-sectional side view of still another alternate embodiment of the catheter introduction syringe.

FIG. 9 shows still another alternate embodiment of a two piece needle generally indicated as 200 including a first or exterior and second or interior portion indicated as 202 and 204 respectively. The first portion or section 202 including a piercing point 206 extends outwardly from the hollow barrel tip generally indicated as 208. The second portion or section 204 extends inwardly from hollow barrel tip 208 into the hollow substantially cylindrical syringe barrel 12. An aperture 210 is formed through the second portion 204 adjacent the distal end of the hollow substantially cylindrical syringe barrel 12. The hollow barrel tip 208 comprises a first barrel tip section or needle hub 214 and a second barrel tip section 216 operatively receiving and supporting the first and second portion 202 and 204 respectively. An intermediate channel 218 including a conical alignment recess 220 is cooperatively formed between the first and second barrel tip sections 214 and 216 in coaxial alignment with the first or exterior portion 202 and second or interior portion 204.

As shown in FIG. 9, when the substantially cylindrical plunger 14 is fully advanced within the hollow substantially cylindrical syringe barrel 12, the major portion of the second or interior portion 204 is disposed within the centrally disposed channel 32 with the inner end 222 thereof disposed adjacent the valve assembly 28.

Otherwise the operation of the embodiment shown in FIG. 9 is similar to the embodiment shown in FIGS. 1 and 2.

Figure 10:
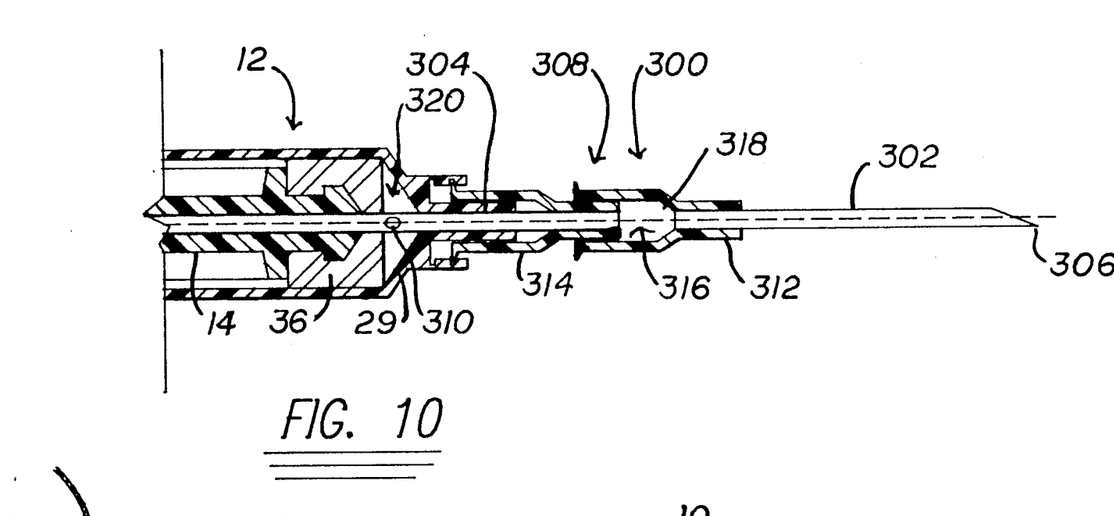
FIG. 10 is a partial cross-sectional side view of yet another alternate embodiment of the catheter introduction syringe.

FIG. 10 shows yet another alternate embodiment of a two piece needle generally indicated as 300 including a first or exterior and second or interior portion indicated as 302 and 304 respectively. Although the structure appears most similar to that disclosed in FIG. 9, the structural and functional variations of FIG. 10 are equally applicable to all the various embodiments. The first portion or section 302 including a piercing point 306 is affixed to the hollow barrel tip generally indicated as 308. The first portion or section 302 extends outwardly from the hollow barrel tip 308, while second portion or section 304 extends inwardly from hollow barrel tip 308 into the hollow substantially cylindrical syringe barrel 12. An aperture 310 is formed through the second portion 304 adjacent the distal end of the hollow substantially cylindrical syringe barrel 12. The hollow barrel tip 300 comprises a first barrel tip section or needle 312 and a second barrel tip section 314 operatively receiving and supporting the first and second portions or sections 302 and 304 respectively. An intermediate channel 316 including a conical alignment recess 318 is cooperatively formed between first and second barrel or sections 312 and 314 in coaxial alignment with the first or exterior portion 302 and second or interior portion 304.

As shown, a chamber 320 is cooperatively formed between the plunger seal 36 and the inner end 29 of the hollow barrel tip 18 when the substantially cylindrical plunger 14 is fully extended. In this configuration, the aperture 310 is disposed within the chamber 320.

In use, the piercing point 306 enters the blood vessel. When entering an artery, the arterial blood pressure causes the substantially cylindrical plunger 14 to retract as the blood enters the chamber 320 through the aperture 310. When cannulating a vein, the catheter introduction syringe 10 is aspirated by the retraction of the substantially cylindrical plunger 14 to create a vacuum or negative pressure within the chamber 320 permitting fluid to pass into the interior of the substantially cylindrical syringe barrel 12 through the aperture 310.

Otherwise the operation of the embodiment shown in FIG. 10 is similar to the other embodiments.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A catheter introduction syringe for the introduction of a catheter or catheter guide wire into a patient's body, said catheter introduction syringe comprises a hollow syringe barrel including a fluid chamber, a plunger movable between an advanced position defining a distal end and retracted position defining a proximal end and slidably disposed within said fluid chamber, a guide passage means formed longitudinally through and engaged with a distal end of said hollow syringe barrel and said plunger, said guide passage means including an aperture disposed within said fluid chamber and a valve assembly disposed in operative relationship relative to said guide passage means to prevent passage of fluid through said guide passage means during flushing or aspirating of said catheter introduction syringe or during the introduction or withdrawal of a catheter or catheter guide wire through said guide passage means and to permit fluid to flow from the patient's body into said fluid chamber through said aperture, said guide passage means being configured to maintain the catheter or catheter guide wire in a substantially straight configuration while the catheter or catheter guide wire is disposed within said guide passage means.

2. The catheter introduction syringe of claim 1 wherein said aperture is formed adjacent the distal end of said fluid chamber.

3. The catheter introduction syringe of claim 1 wherein said guide passage means comprises a first section extending outwardly from said hollow syringe barrel and a second section extending inwardly into the interior of said fluid chamber.

4. The catheter introduction syringe of claim 3 wherein said second section extends inwardly from the inner end of said first section.

5. The catheter introduction syringe of claim 4 wherein said first section and said second section comprise a single hollow member.

6. The catheter introduction syringe of claim 3 wherein an intermediate channel is formed between said first section and said second section.

7. The catheter introduction syringe of claim 6 further including a conical alignment recess formed on the proximal end of said first section.

8. The catheter introduction syringe of claim 3 wherein said guide passage means further includes a conical alignment recess formed on the proximal end of said second section.

9. The catheter introduction syringe of claim 3 wherein the proximal end of said second section is disposed within said plunger when said plunger is fully retracted relative to said hollow syringe barrel.

10. The catheter introduction syringe of claim 9 further includes a plunger seal mounted on said plunger and a plunger stop is formed on the interior of said hollow syringe barrel to engage said plunger seal to limit retraction of said plunger when said plunger is fully retracted relative to said hollow syringe barrel.

11. The catheter introduction syringe of claim 1 wherein said plunger includes a valve recess formed therethrough and said valve assembly is operatively disposed therein.

12. The catheter introduction syringe of claim 1 wherein a chamber is cooperatively formed between the distal end of said plunger and the distal end of said hollow syringe barrel when said plunger is fully advanced, said aperture being disposed within said chamber.

13. A catheter introduction syringe for the introduction of a catheter or catheter guide wire into a patient's body, said catheter introduction syringe comprises a hollow syringe barrel including a fluid chamber, a plunger movable between an advanced position defining a distal end and retracted position defining a proximal end and slidably disposed within said fluid chamber, a guide passage means formed longitudinally through said hollow syringe barrel and said plunger, said guide passage means including a first and second section, said first section including a piercing point extending outwardly from the distal end of said hollow syringe barrel and said second section having an aperture formed therethrough to selectively communicate with said fluid chamber is affixed to said plunger slidably disposed within said first section and a valve assembly disposed in operative relationship relative to said guide passage means to prevent passage of fluid through said guide passage means during flushing or aspirating of said catheter introduction syringe or during the introduction or withdrawal of a catheter or catheter guide wire through said guide passage means and to permit fluid to flow from the patient's body into said fluid chamber through said aperture, said guide passage means being configured to maintain the catheter or catheter guide wire in a substantially straight configuration while the catheter or catheter guide wire is disposed within said guide passage means.

14. The catheter introduction syringe of claim 13 wherein said aperture is formed through said second section adjacent the distal end of said plunger.

15. The catheter introduction syringe of claim 14 wherein said second section includes a conical alignment recess formed on the proximal end thereof.

16. The catheter introduction syringe of claim 13 wherein the major portion of said second section is disposed within said first section when said plunger is fully advanced inwardly relative to said hollow syringe barrel.

17. The catheter introduction syringe of claim 16 further includes a plunger stop is formed on the interior of said hollow syringe barrel to engage said plunger seal to limit retraction of said plunger when said plunger is fully retracted relative to said hollow syringe barrel.

18. The catheter introduction syringe of claim 13 wherein the distal end of said second portion is disposed within said first section when said plunger is in either the fully advanced or fully retracted position relative to said hollow syringe barrel.

19. The catheter introduction syringe of, claim 13 wherein said plunger includes a valve recess formed therethrough and said valve assembly is operatively disposed therein.

20. The catheter introduction syringe of claim 13 wherein a chamber is cooperatively formed between the distal end of said plunger and the distal end of said hollow syringe barrel when said plunger is fully advanced, said aperture being disposed within said chamber.

21. A catheter introduction syringe for the introduction of a catheter or catheter guide wire into a patient's body, said catheter introduction syringe comprises a hollow syringe barrel including a fluid chamber, a plunger movably between an advanced position defining a distal end and retracted position defining a proximal end and disposed within said fluid chamber, a guide passage means formed longitudinally through said hollow syringe barrel and said plunger, said guide passage means including a first and second section, said first section including a blunt point extending outwardly from the distal end of said hollow syringe barrel and said second section having an aperture formed therethrough to selectively communicate with said fluid chamber and including a piercing point affixed to said plunger slidably disposed within said first section and a valve assembly disposed in operative relationship relative to said guide passage means to prevent passage of fluid through said guide passage means during flushing or aspirating of said catheter introduction syringe or during the introduction or withdrawal of a catheter or catheter guide wire through said guide passage means and to permit fluid to flow from the patient's body into said fluid chamber through said aperture, said guide passage means being configured to maintain the catheter or catheter guide wire in a substantially straight configuration while the catheter or catheter guide wire is disposed within said guide passage means.

22. The catheter introduction syringe of claim 21 wherein said aperture is formed through said second section adjacent the distal end of said plunger.

23. The catheter introduction syringe of claim 21 said second section includes a conical alignment recess formed on the distal end thereof.

24. The catheter introduction syringe of claim 21 wherein the major portion of second section is disposed within said first section and said piercing point extends outwardly from said blunt point when said plunger is fully advanced relative to said hollow syringe barrel.

25. The catheter introduction syringe plunger of claim 24 wherein said blunt point is disposed within the first section when said plunger is fully retracted relative to said hollow syringe barrel.

26. The catheter introduction syringe of claim 25 further includes a plunger seal mounted on said plunger and a plunger stop is formed on the interior of said hollow syringe barrel to engage said plunger seal to limit retraction of said plunger when said plunger is retracted relative to said hollow syringe barrel.

27. The catheter introduction syringe of claim 21 wherein said plunger includes a valve recess formed therethrough and said valve assembly is operatively disposed therein.

28. The catheter introduction syringe of claim 21 wherein a chamber is cooperatively formed between the distal end of said plunger and the distal end of said hollow syringe barrel when said plunger is fully advanced, said aperture being disposed within said chamber.

* * * * *